United States Patent [19]

Berg et al.

[11] 4,290,011
[45] Sep. 15, 1981

[54] PARTICLE LENGTH AND VOLUME COMEASUREMENT WITH CONTROLLED ORIENTATION

[75] Inventors: Robert H. Berg, Elmhurst; Richard F. Karuhn, Downers Grove, both of Ill.

[73] Assignee: Particle Data, Inc., Elmhurst, Ill.

[21] Appl. No.: 907,010

[22] Filed: May 18, 1978

[51] Int. Cl.³ ............................................ G01N 27/00
[52] U.S. Cl. ............................................ 324/71 CP
[58] Field of Search .............. 324/71 CP; 235/92 PC; 365/555

[56] References Cited

U.S. PATENT DOCUMENTS

| | | | |
|---|---|---|---|
| 3,705,348 | 12/1972 | jacobs | 324/71 CP |
| 3,739,268 | 6/1973 | Karuhn et al. | 324/71 CP |
| 3,793,587 | 2/1974 | Thom et al. | 324/71 CP |
| 3,871,770 | 3/1975 | Von Behren et al. | 324/71 CP |
| 3,902,115 | 8/1975 | Hogg et al. | 324/71 CP |
| 3,924,180 | 12/1975 | Salzman et al. | 324/71 CP |
| 4,001,678 | 1/1977 | Berg | 324/71 CP |
| 4,104,611 | 3/1977 | Simpson et al. | 324/71 CP X |
| 4,140,966 | 2/1979 | Godin et al. | 324/71 CP |
| 4,165,484 | 8/1979 | Haynes | 324/71 CP |

FOREIGN PATENT DOCUMENTS 2422129 11/1975 Fed. Rep. of Germany ... 324/71 CP

OTHER PUBLICATIONS

Spielman et al., "Improving Resolution . . . by Hydrodynamic Focusing", Journal of Colloid and Interface Science 26, 1968, pp. 175–182.
Byerly et al., Machine for Rapidly Counting Etc., Rev. of Scien. Inst., vol. 46, No. 5, May 1975, pp. 571–522.
Thom; R., Vergleichende Untersuchungen zur Electronischen Zellvolumen-Analyse, Telefunken (Chap 6)-Translation Nov. 1976.

*Primary Examiner*—Gerard R. Strecker
*Attorney, Agent, or Firm*—Hill, Van Santen, Steadman, Chiara & Simpson

[57] ABSTRACT

A method of and means for controlling orientation of particles through a sensing zone in a particle analyzing system, which facilitates particle shape determination, comprises laminar flow orientation of the particles in a stream moving through an elongate straight passage coaxially aligned with an elongate sensing zone longer than the longest particle to be sensed and analyzed. The particles are carried through the sensing zone in an isokinetic laminar flow sheath of fluid.

20 Claims, 7 Drawing Figures

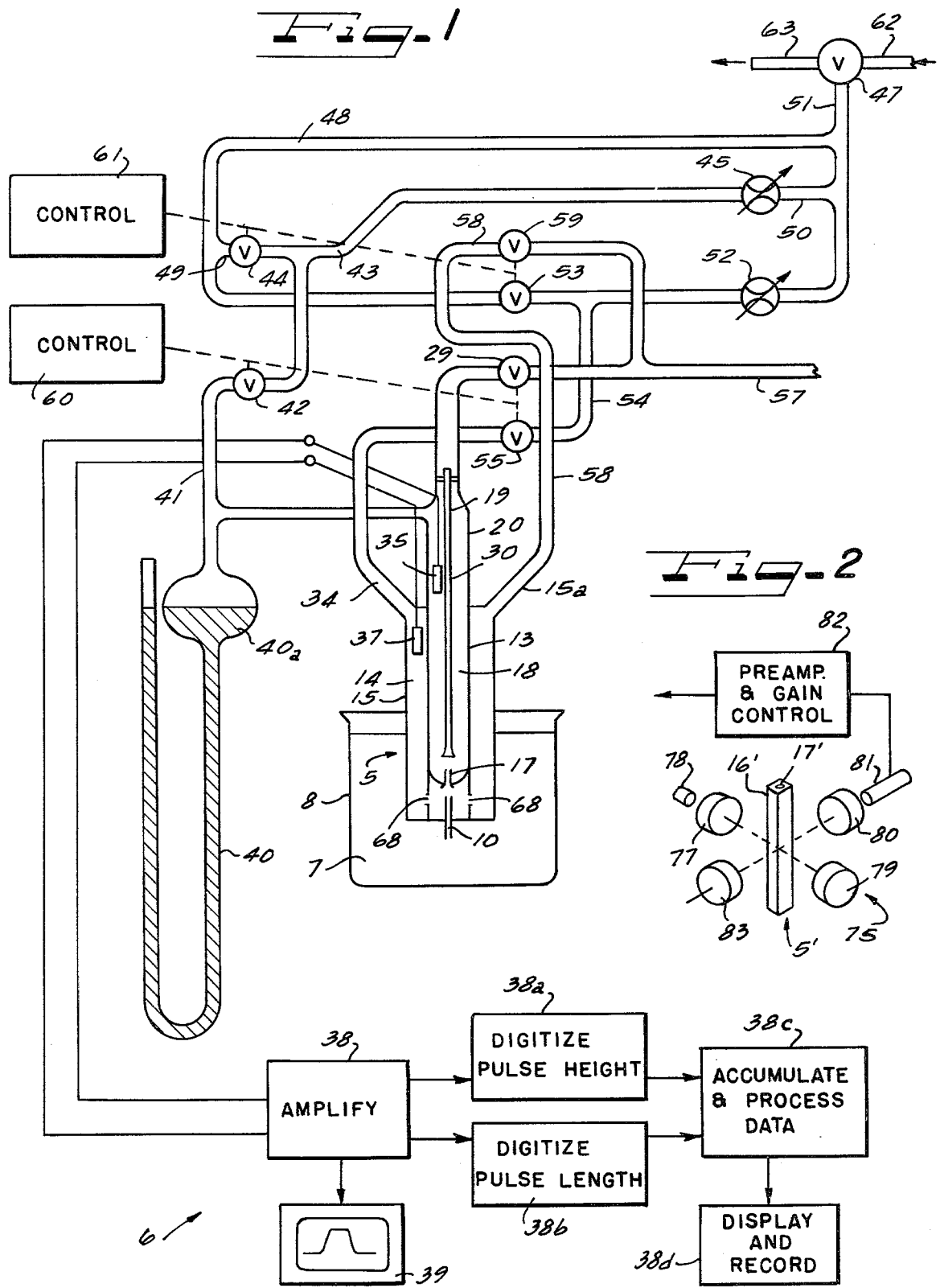

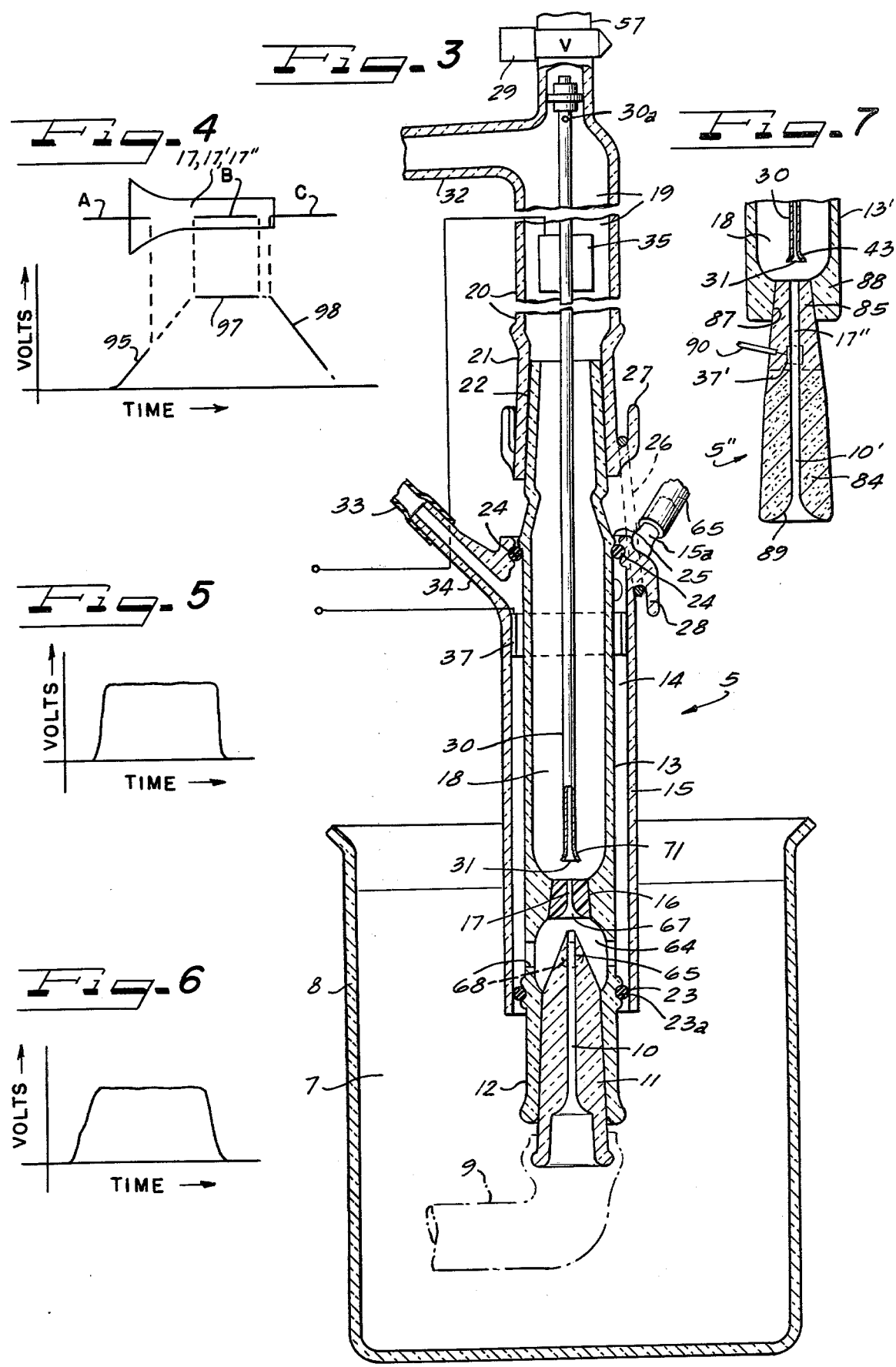

PARTICLE LENGTH AND VOLUME COMEASUREMENT WITH CONTROLLED ORIENTATION

This invention is concerned with improvements in isokinetic sampling in particle analysis systems, and is more particularly concerned with a method of and means for controlling orientation of particles to facilitate particle shape determination while passing through the sensing zone of the particle analyzing system.

Substantial advances have been made in isokinetic, i.e., equal motion sampling and controlled particle orientation for particle analysis techniques, both those involving photic sensing zone and those involving electrolytic sensing zones. Considerable attention has been given to attain improved fidelity of particle dimension-related signals caused by particle passage through a given sensing zone. An example of an important advance in this direction is found in Robert H. Berg, U.S. Pat. No. 4,001,678 entitled "Displacement Metering With Independent Ancillary Flow". Therein is taught how to attain improved fidelity of particle dimension response in particle sensing or counting apparatus by so-called hydrodynamic focusing in a sensing orifice in one of a pair of tubes immersed in a bath of particle-free electrolyte and utilizing independently controlled coaxial flows, substantially accurately proportioned between filamentary and sheathing flows, maintaining accuracy in particle suspension metering and therefore particle concentration measurement. In that patent an apparatus and method are disclosed especially useful in association with particle sensing counting and analyzing instruments of the kind available from the assignee of the present application, Particle Data, Inc., under the trademarks "ElectroZone", "CELLOSCOPE" and "ELZONE". Such apparatus operates on the principle of passing a sample of electrolyte with entrained particles through an orifice providing a properly constricted path for an electrical current. Sensing of particles flowing through the orifice is effected by modulation of the electrical current by the particles, such modulation being amplified and suitably recorded, analyzed, visually observed on an oscilloscope, and the like. The measurement of particle lengths by this particle sensing method was initially reported by David R. Kominz in "Correlations of Length and Volume Measurements in Myofibril Suspensions", Biophysical Journal, Vol. II, 1971, pp 47-65. However, in spite of the substantial improvements attained according to the teachings of the aforesaid patent, there has still been some problem in achieving accurate particle length and shape determinations.

We have discovered a practical, simple and efficient method of and means for solving that problem, and by which throughout an analytical time span in a fluid filled circuit elongated particles are handled in a manner effectively free from turbulence, continuously and sequentially in isokinetic laminar flow, i.e. all particle bearing fluid moving in the same direction with substantially imperceptible velocity gradient.

To this end, the present invention provides a method of controlling the presentation of particles to a sensing zone to facilitate particle shape determination in a particle analysis system of a type responsive to electrical signals generated by particles passing through the sensing zone, comprising transporting the particles in a laminar flow stream through a first elongate passage of sufficient length to cause stable orientation of the particles longitudinally in that passage, transferring from the stream of longitudinally oriented particles from the downstream end of said first passage in isokinetic presentation to the entrance of a coaxially aligned second elongate straight sensing zone passage of greater length than the longest particle to be analyzed, and advancing the isokinetic particle bearing stream through said sensing zone passage in laminar flow manner so as to maintain the particles in their stable longitudinal orientation for particle shape determination as the particles generate electric signals while tranversing the length of said sensing zone.

For practice of the method, the present invention provides means for controlling the presentation of particles to a sensing zone to facilitate particle shape determination in a particle analysis system of a type responsive to electrical signals generated by particles passing through the sensing zone, comprising a first elongate passage for transporting therethrough particles in a laminar flow stream, the passage being of sufficient length to cause stable orientation of the particles longitudinally in the passage; a second elongate straight sensing zone passage of greater length than the longest particle to be analyzed, said second passage having an entrance coaxially aligned with the downstream end of said first passage; said passages being so oriented that the stream of longitudinally oriented particles from the downstream end of said first passage is transferred in isokinetic presentation to said entrance of the second passage; and means for effecting advance of the isokinetic particle bearing stream through said second passage in laminar flow manner so as to maintain the particles in their longitudinal orientation for particle shape determination by means of electrical signals generated by the particles while traversing the length of the sensing zone.

Other objects, features and advantages of the invention will be readily apparent from the following description of representative embodiments thereof, taken in conjunction with the accompanying drawings, although variations and modifications may be effected without departing from the spirit and scope of the novel concepts embodied in the disclosure, and in which:

FIG. 1 is a schematic illustration of a particle analysis system of the electric current modulation pulse generation method, embodying principles of the present invention.

FIG. 2 is a schematic adaptation for photic zone detection of particles in the practice of the present invention.

FIG. 3 is a fragmental vertical sectional detail view showing a representative form of apparatus providing cooperative particle orientation and sensing zone passages for accurate particle shape determination according to the principles of the present invention.

FIG. 4 is a schematic illustration showing the relationship of rod like particle traversing through the sensing zone of the apparatus of FIGS. 1, 2 and 7 relative to pulse curve observable on an oscilloscope.

FIG. 5 schematically illustrates a pulse curve generated by a generally spherical particle as observed on an oscilloscope.

FIG. 6 schematically illustrates a pulse curve generated by a relatively flattened or disk-shape particle as observed on an oscilloscope.

FIG. 7 illustrates a modified embodiment of the particle orientation and sensing zone passages within the principles of the present invention.

By way of example, the principles of the present invention may be embodied in displacement metering apparatus 5 (FIGS. 1 and 3) embodying significant improvements over the disclosure in the aforesaid U.S. Pat. No. 4,001,678. To any extent necessary disclosure of that patent is incorporated herein by reference. The apparatus 5 is especially adapted for use in a sensing system 6, often referred to as particle counter, where accurate isokinetic sample metering is essential. Particle-entraining liquid electrolyte may be supplied for analysis from a suitable particle suspension source such, for example, as may be contained in a supply chamber 7 in a container or beaker 8 or from any other source through a conduit 9. From the supply chamber 7 the particle entraining liquid is transported in a laminar flow stream through an elongate, preferably straight particle aligning first passage 10 of sufficient length to cause stable orientation of particles longitudinally in the direction of flow in that passage. In a convenient construction the passage 10 is adapted to extend through a plug member 11 coupled into a tubular lower end fitting extension 12 of a preferably test tube-like container 13 defining a double walled chamber 14 with a larger diameter tubular container 15. Mounted adjacently above the downstream end of the passage 10 is an orifice plug member 16 providing a second elongate straight sensing zone passage 17 of greater length than the longest particle to be analyzed. The passage 17 has its upstream end in spaced coaxial alignment with the passage 10 and its downstream end discharging into an elongate chamber 18 within the container 13. Although the plug member 11 may be formed from glass, using usual glass fabricating techniques, the orifice member 16 is preferably made from a material in which the passage 17 can be held to substantially accurate diameter throughout its sensing zone length, a solid polymeric material such as Delrin having been found suitable for the purpose. Such a material can readily be drilled to form the passage 17 in the small multi-micron diameter appropriate for the desired particle analysis.

While the containers 13 and 15 may be formed in an integral one piece arrangement, they are preferably two separate generally telescopically related hollow parts to facilitate separation and cleaning. Leading upwardly from the chamber 18 is a passage 19 provided by a vertical member 20 supported in any desirable manner. At their upper ends the containers 13 and 15 are secured to the lower end portion of the member 20, preferably detachably for cleaning purposes. A tapered fitting terminal 21 on the lower end of the member 20 may receive a complementarily shaped head 22 at the upper end of the container 13, such as in a standard glass joint. A fluid tight coupling of the tubular container 15 with the inner container 13 may be by means of an O-ring 23 adjacent to the lower end of the member 15 engaging in an annular shoulder groove 23a on the container 13, and an O-ring 24 adjacent the upper end of the member 15 engaging an annular shoulder 25 on the member 13. Means comprising one or more resilient bands 26 engage anchoring hooks 27 and 28 on respectively the lower end of the member 20 and the upper end of the member 15 and draw the members together whereby to maintain the assembly in operatively tight but separable connection.

At its upper end, the passage member 20 has a valve 29 which controls connection of the passage 19 and the chamber 18 with a suitable vacuum source by way of a relatively small diameter vertical suction tube 30 having at its lower end a suction port 31 axially aligned in adjacent spaced relation to the downstream or exit end of the passage 17. Leading off from the member 20 adjacently below where the upper end of the tube 30 is secured, is a branch duct 32 leading to means for supplying fluid to and for effecting displacement of fluid in the chamber 18. A line 33 communicates a source of fluid through a passage branch 34 extending from the upper portion of the member 15 to communicate with the chamber 14. The various connecting joints and couplings of the system are constructed to be unyielding to pressure differences as high as desired in use, and the entire internal circuit of passageways and chambers is fluid-filled. A pin hole 30a in the upper end of the tube 30 provides a bleed-off for any entrapped air in that area. A branch 15a on the member 15 at the upper end of the chamber 14 may serve to bleed air from that area. If preferred, and especially for handling of heavier particles, orientation of the apparatus just described may be inverted so that the passage 10 delivers downwardly to the passage 17. In such a rearrangement the air pocket bleedoffs will have to be reoriented.

Sensing of particles flowing through the sensing zone passage 17 is effected by modulation of an electrical current by the particles, generating pulses which are amplified and suitably recorded, totalized, visually observed on an oscilloscope, and the like. For this purpose, an electrode 35 is located in suitable operative relation to the chamber 18 such as in the adjacent portion of the passage 19 so as to be effective at the downstream or discharge end of the passage 17. An electrode 37 is located in the chamber 14 to be effective at the upstream or entry end of passage 17. This provides for electronic connection with the appropriate analyzing instrumentalities of the system 6 represented schematically as including an amplifier 38 with which is connected a oscilloscope 39 for visual observation of pulses generated by particles traversing the sensing zone passage 17. From the amplifier 38 the pulses are received in means 38a for digitizing the pulse height, and means 38b for digitizing pulse length. From the digitizing means 38a and 38b the pulse signals pass to a data accumulator and processing analyzer 38c for data accumulation and processing. Connected with the analyzer 38c are suitable means 38d such as a counter, computer, or the like, to provide a display record.

Representative hydraulic operating and flushing circuitry for the apparatus 5 comprises a vacuum gauge shown in this instance as a U-shaped metering siphon or manometer 40 which may be on the order of that described in Berg U.S. Pat. No. 3,481,202, and is operatively connected at its upper end to the branch duct 32. Leading from that connection is a hydraulic line 41 having therein a three-way valve 42 and communicating with a hydraulic line 43 having a three-way valve 44 at one side of the connection of the line 43 with the line 41 and a flow regulating valve 45 at the other side of the connection of the line 43 with the line 41. At its opposite ends, the line 43 is connected in circuit with a diluent supply controlling and venting valve 47 by way of a loop circuit 48 connected at an intermediate point by a branch 49 with the line 43 adjacent to the valve 44 and by means of an opposite intermediate branch 50 with the line 43 adjacent to the valve 45. At one side of the loop circuit 48 as divided by connection with the line 43, communication by means of a branch 51 is effected with the diluent and vent valve 47. In the other half of the loop circuit 48 a flow regulating valve 52 is located adjacent to the branch 50 and a two-way valve 53 is located in the loop on the other side of branch line 54 which communicates with the loop between the valves 52 and 53 and leads to a three-way valve 55 for controlled communication with the duct 33 which is connected to the sheathing flow supply branch 34 leading to the chamber 14 of the apparatus. A hydraulic line 57 leads from a vacuum source through the three-way valve 29 to the vacuum end of the member 20 and the tube 30. A branch hydraulic connecting line 58 is connected in communication with the bleedoff branch 15a leading from the member 15. A two-way valve 59 is in control of the line 58. A common control 60 is desirably provided for the valves 29, 42 and 55. A common control 61 is desirably provided for the valves 44, 53 and 59. The valve 47 may have an independent control. Each of the regulating valves 45 and 52 may be independently adjustable for regulating flow through its associated hydraulic line.

In an operating cycle of the apparatus 5, particles passing through the sensing zone passage 17 are analyzed for a number of characteristics such as shape, mass or particle unit volume, number of particles per unit volume of carrier liquid, and particle length. For some kinds of particles length is a critical characteristic. For example, it may be desirable to determine what percentage of particles in an isokinetic sample are of a particular length and/or shape. Determination as to the concentration of particles having identifiable length in an isokinetic sample may be desired, as for example asbestos particles when testing for enviromental contamination.

We have discovered that much improved analytical results are obtained by having the passage 10 of sufficient length, considered with regard to the flow velocity of the filamentary stream in which the particles in an isokinetic sampling are transported, to orient the particles longitudinally in the passage. The filamentary stream of longitudinally oriented particles is then transferred a limited distance from the downstream end of the orientation passage 10 into the sensing zone passage 17 across a subchamber 64 where the filamentary stream is enveloped in a laminar flow sheath of particle free fluid. To enhance laminar sheathing of the filamentary stream of particles the plug member 11 has a conical sharp edged tip portion 65 extending into and to a substantial extent through the subchamber 64 toward the upstream end of the passage 17. Entry into the passage 17 is preferably through a flared smoothly contoured bellmouth entrance 67 the surface of which is desirably slightly arched to a smooth inner end transition into the straight sensing zone part of the passage 17.

For isokinetic sampling, the apparatus 5 is conditioned to effect a low pressure differential in the chamber 18 relative to the supply chamber 7 and the sheathing fluid chamber 14 so that a predetermined volume of particle carrying electrolyte will be drawn from the supply chamber 7 through the orientation passage 10 at sufficient velocity and electrolyte entrainment to attain the desired longitudinal separation and lengthwise orientation of the particles transported in filamentary stream through the passage 10. Integrity of the filamentary particle stream is maintained in the transition interval between the downstream end of the passage 10 and the upstream end of the passage 17, aided by enveloping the filamentary stream isokinetically in a laminar nonturbulent flow sheath of clear fluid in the chamber 64 supplied from the chamber 14 by way of ports 68 in the wall of the member 13. As each particle traverses the length of the passage 17, the pulse signal generated by it is amplified, analyzed, variously discriminated and recorded in the sensing system 6, such as for number per unit volume of isokinetic sample, relative or proportional sizes, shapes, length and the like.

Waste particles leaving the exit end of the passage 17 are efficiently collected and drawn off in isokinetic manner into the suction catcher conduit tube 30 through the suction port 31 which is desirably defined by a flared smoothly contoured bellmouth 71 and avoids hangup of waste particles. Suction attained by connection of the suction or catcher tube 30 with vacuum source by opening the valve 29 not only draws into the port 31 the waste particle stream leaving the passage 17, but also ambient fluid in the chamber 18 which sheaths the waste particles in a flush-flow stream and substantially prevents migration of any particles therefrom in the interval between the passage 17 exit and the suction port 31. This prevents spent particles from circulating in that area, and avoids modulation aberrations from possible turbulence in the chamber 18, assuring achievement of a high degree of accuracy in the sensing zone analysis.

In operation, assuming that the supply chamber 7 has a fill of electrolyte carrying particles to be analyzed, and the remainder of the system is prepared for isokinetic sampling, the valve control 60 is actuated to open the valves under its control, namely the valves 29, 42 and 55, and the valve control 61 is actuated to close the valves 44, 53 and 59 under its control, and the valve 47 is actuated to connect a diluent input line 62 through the branch 51 with the loop circuit 48. Since the suction tube 30 is now connected with vacuum source, isokinetic sampling proceeds at a controlled rate and as long as desired to complete the analysis. When it is desired to fill and flush the system, the valves 29, 42 and 55 are controlled by the controller 60 to be in the open position, the valves 44, 53 and 59 controlled by the controller 61 are actuated to be in the open position, and the valve 47 is in the diluent connecting position.

For draining the system, all of the valves 29, 42 and 55 and the valves 44, 53 and 59 are open, and the valve 47 is actuated into the vent position, venting through a line 63.

For back flushing, the valve control 60 is operated to close the valves 29, 42 and 55, the valve control 61 is operated to open the valves 44, 53 and 59, and the valve 47 is operated to open the system to diluent input through the line 62. Should it be desired to clean out the diluent supply lines 33, 54 and the upstream portion of the passage 17, the valve controller 60 may be operated to close the valve 42 and open the valves 29 and 55 while the valves 44, 53 and 59 remain closed, and the valve 47 is opened to the vent side 63 and closed to the diluent input side 62.

Instead of electrical current modulation or electrolytic zone sensing of particles in the sensing zone passage 17, other types of sensors may be employed such as a sonic zone sensor wherein a particle is detected by reflection of an ultrasonic beam in a liquid medium, or other types of devices operative to generate pulses which vary in amplitude according to a particular parameter. By way of example, a photic zone sensor 75

(FIG. 2) may be located in cooperation with the sensing zone orifice member 16 of displacement metering apparatus 5'. For this purpose the member 16' is transparent so that particles travelling through the sensing zone passage 17' will be illuminated by a beam of light from a lens assembly 77 in front of a light source 78 with a light trap 79 having a black light absorbent surface disposed in the path of the beam on the opposite side of the member 16'. Light reflected from particles passing through the sensing zone passage 17' is transmitted through a lens assembly 80 to the face of a photomultiplier tube 81 which applies signals to a pre-amp and gain control circuit 82. A light trap 83 is disposed opposite the sensing zone 17' on the axis of the lens assembly 80 and the photomultiplier 81, to provide a dark background. This type of sensor may also be used with the light source disposed opposite the light sensing means, and with pulses being thereby generated in respect to particles blocking the light. Such a photic zone sensor is described, for example, in Berg et al U.S. Pat. No. 3,345,502.

In the modification of FIG. 7, the apparatus 5" is a simplified version of the apparatus 5 which has already been described. For determining the shape of some types of particles it may not be necessary to provide a clear fluid sheathing of the laminar flow particle-carrying stream in transition between the particle orienting first passage and the second sensing zone passage. Accordingly, all of the structure involving the tubular container 15 and the sheathing flow supply chamber 14 of the apparatus 5 of FIGS. 1 and 3 can be eliminated, while the remainder of the apparatus and the sensing system 6 may remain the same. In this modified arrangement an elongate combined orientation passage and sensing zone passage member 84 which has a tapered end portion 85 fits snugly in a complementary tapered coaxial bore 87 in a base end portion 88 of the modified tubular member 13'. Axially within the member 84 is a first, particle orienting passage 10' into which leads a smoothly contoured bellmouth entrance 89 at the free end of the member 84. The arrangement is such that particle containing suspension is drawn from a source which may be supplied in a chamber such as the chamber 7 in a beaker 8 demonstrated in FIG. 3. The orientation passage 10' is dimensioned both in cross sectional flow area and in length to assure stable orientation of the particles longitudinally in the passage as the particles are transported in a laminar flow stream of the electrolytic fluid in which the particles are carried. According to well known hydraulic principles, the velocity of a stream in laminar flow through a passage is greater at the center of the passage due to the drag of the passage walls on the perimeter of the stream. Accordingly as the stream is caused to traverse the orientation passage 10' the particles are caused to assume a stable longitudinal orientation in the stream.

From the first particle orientation in the passage 10' the particles pass immediately into a second elongate straight sensing zone passage 17" of greater length than the longest particle to be analyzed, such second passage being, in effect, a continuation of the passage 10' and having its upstream or entrance coaxially aligned with the downstream end of the first passage 10'. Although the electrode 37' may be oriented relative to the member 84 in the manner of the electrode 37 in FIG. 3, in this instance, the electrode 37', corresponding to the electrode 37 in FIGS. 1 and 3, is shown as mounted in the member 84 at the entrance into the sensing zone passage 17" and is properly shaped for the intended purpose. Leading from the electrode 37' is an insulated electrical lead wire 90 unaffected by immersion in the particle suspension electrolyte into which the member 84 extends in use. It will be understood that the cooperating electrode will correspond to the electrode 35 in FIGS. 1 and 3. Similarly as described in connection with the sensing zone passage 17 in FIGS. 1 and 3, the particles flowing through the sensing zone passage 17' effect modulation of an electrical current, thus generating pulses which are amplified and suitably recorded, totalized, visually observed and the like in the same manner as described in connection with FIGS. 1 and 3. If additional sheathing of the filamentary stream in a laminar flow sheath of particle free fluid is desired, at least that portion of the member 84 upstream from the electrode 37' may be made of a suitable porous material such that as the stream is caused to traverse the coaxial passages 10' and 17", electrolyte free and clear of particles may be drawn through the porous filter wall of the member 84 into the passage 10'. Isokinetic action is effected similarly as in FIGS. 1 and 3 by suction applied through the suction and catcher tube 30 which has its entrance port in alignment with the exit from the passage 17" in substantially the same orientation and for the same purpose as already described hereinbefore.

Substantial accuracy as to particle length as well as shape discrimination are attained not only for recording but also for instantaneous visual observation by way of unique substantially trapezoidal pulse patterns on the screen of the oscilloscope 39, during the smooth, sheathed passage of up to thousands of particles per minute through the sensing zone passsage 17, 17', or 17". For example, FIG. 4 demonstrates the sharp, strong, particle length pulses observable on the oscilloscope 39 as linear, i.e., rod-like fiber-like, prolate spheroid, particles traverse the sensing zone passage 17, 17' or 17" seriatim. Illustratively, three particle positions A, B and C are shown. In position A, as the particle passes the entrance into the sensing zone, progress of the particle is observable as an ascending substantially diagonal pulse line or ramp 95 which travels upwardly a substantially straight line, the ramp time representing the length of the particle. In position B the particle is completely within the detection zone in the passage 17 whereupon the pulse shape or curve flattens off as shown at 97, the amplitude of which represents the volume of the particle. Then as the particle exits from the passage 17, 17' or 17" as illustrated by the position C, the pulse signal ramps in a substantially straight line diagonally downwardly as indicated at 98, which ramp time also representing the length of the particle.

Where particles in shapes other than linear pass through the sensing zone passage 17, 17' or 17" the pulse shapes observed on the oscilloscope will differ from the FIG. 4 straight line angular pulse ramps of the linear particles. Hence, during isokinetic sampling in the apparatus 5, 5' or 5", involving diverse particles, linear particles can be discriminated from non-linear. For example, as depicted in FIG. 5, generally spherical, i.e., orthospheroid, ball-like, particles will be observed on the oscilloscope to produce a pulse shape of rather trapezoidal form rising substantially vertically at the entry end, then flattening at the top while the particle is fully in the sensing zone, and then dropping off substantially vertically at the departure or exit end with only slight transition curvatures at top and bottom of the vertical legs.

FIG. 6 demonstrates pulse shape observable when a particle of oblate spheroid shape, i.e., flake, disk of any of various relative thicknesses, or similar shape, traverses the sensing zone passage. As such a particle enters the sensing zone the oscilloscope pulse shape display will show a generally flat S or ogee slanting upward curve to a relatively flat horizontal top while the particle is fully in the sensing zone and then dropping off with a flat S or ogee curve as the particle leaves the sensing zone.

As to any of the particle identifying pulse shapes as represented in FIGS. 4, 5 and 6, particle volume may also be discriminated by the pulse height. Thus the orthospheroid particles may show substantially greater pulse height than extreme prolate spheroid or extreme oblate spheroid particles, although within each of those categories there may be variations in particle volume. Thus a substantial range of analytical results can be obtained not only in discrimination as to categories of particles but also as to determination of dimensional parameters within categories, where desirable.

It will be understood that variations and modifications may be effected without departing from the spirit and scope of the novel concepts of this invention.

We claim as our invention:

1. A method of controlling the presentation and traverse of elongated particles in fluid suspension to and through a sensing zone of greater length than the longest particle to be analyzed, to facilitate particle shape or size determination in a particle analysis system of a type responsive to electrical signals generated by particles passing through said sensing zone during an analytical time span, comprising:
   effecting in a fluid-filled circuit all of the following steps in a manner effectively free from turbulence, continuously and sequentially in isokinetic laminar flow;
   (a) transporting the particles through a first elongate passage of sufficient length to cause stable longitudinal orientation of the particles in a filamentary stream in said passage;
   (b) transferring said filamentary stream of longitudinally oriented particles as a core stream enveloped in a particle-free cotraveling fluid sheath from the downstream end of said first passage and smoothly, and without disturbing the stable longitudinal orientation of the elongated particles, receiving said stream through the entrance end of a coaxially aligned sensing zone passage;
   (c) advancing said fluid sheathed core stream through said sensing zone passage and maintaining the particles in said stable longitudinal orientation for particle shape or size determination as the particles generate signals while traversing the length of said sensing zone;
   (d) discharging said fluid sheathed core stream of now waste particles from an exit end of said sensing zone passage into a continuation of said fluid filled circuit;
   (e) controlling the flow of the stream of waste particles in movement away from said exit end and thus avoiding straying, hangup or recycling of the waste particles relative to said exit end;
   (f) and applying a constant differential pressure throughout said fluid filled circuit in effecting all of the foregoing steps during said analytical time span.

2. A method according to claim 1, wherein said passages are continuous in alignment with one another, and transporting the isokinetic particle bearing stream across an electrode at the entrance into said sensing zone passage.

3. A method according to claim 1, wherein said first elongate passage extends through a porous member, and effecting a laminar flow sheath said longitudinally oriented particle core stream by receiving particle free fluid into said passage through the porous wall of said member.

4. A method according to claim 1, comprising effecting said controlling by enclosing said fluid sheathed core stream of waste particles in a second particle-free fluid sheath derived from sheathing fluid surrounding said exit end, and catching said fluid sheathed core stream of waste particles in a smoothly bellmouth shaped catcher port in coaxial adjacently spaced relation to said exit end.

5. A method according to claim 1, which comprises providing the entrance end of said sensing zone passage with a flared smoothly contoured bellmouth which opens concentrically towards the downstream end of said first passage, and receiving into said sensing zone passage through said bellmouth a particle-free sheathing fluid from a chamber defined about a conically tapered tip terminating in a sharp edged rim at said downstream end and from which the filamentary particle stream from said first passage is isokinetically discharged coaxially toward and into said bellmouth and thus into said sensing zone passage enveloped in sheathing fluid from said chamber.

6. A method according to claim 1, comprising producing electrical signals as substantially trapezoidal pulses generated by the particles traversing the length of said sensing zone and obserably reproducing said signals and thereby identifying the shape parameters of the particles.

7. A method according to claim 1, comprising producing electrical signals as substantially trapezoidal pulses generated by the particles traversing the length of said sensing zone, and by the pulse shapes identifying particle length as well as particle shape.

8. A method according to claim 1, comprising producing electrical signals as substantially trapezoidal pulses generated by the particles traversing the length of said sensing zone, and observably reproducing said signals and by the pulse shapes determining length of particles by pulse duration and volume of particles by pulse amplitude.

9. A method according to claim 1, comprising producing electrical signals as substantially trapezoidal pulses generated by the particles traversing the length of said sensing zone, and observably reproducing said signals and by the pulse shaped discriminating between particles of prolate, oblate and orthospheroid shapes.

10. Apparatus for controlling the presentation and traverse of elongated particles in fluid suspension to and through a sensing zone passage of greater length than the longest particle to be analyzed, to facilitate particle shape or size determination in a particle analysis system of a type response to electrical signals generated by particles passing through said sensing zone during an analytical time span, comprising:
   a fluid-filled circuit for effecting turbulence-free continuous and sequential isokinetic laminar flow, and having:

(a) means defining a first elongate passage of sufficient length for transporting the particles therethrough in stable longitudinal orientation in a filamentary particle stream in said passage;

(b) means for enveloping said filamentary particle stream as a core stream in a particle-free cotraveling fluid sheath;

(c) said sensing zone passage having an entrance end coaxially aligned with a downstream end of said first passage for transference of said sheathed core stream smoothly from said first passage into said sensing zone passage, said entrance end being shaped for avoiding any disturbance in the stable longitudinal orientation of the elongated particles during said transference;

(d) means responsive to the particles for generating electrical signals for particle shape or size determination while the particles advance in said fluid sheathed core stream through said sensing zone passage in said stable longitudinal orientation;

(e) means providing a continuation of said fluid filled circuit into which said fluid sheathed core stream of now waste particles is discharged from an exit end of said sensing zone passage;

(f) means for controlling the flow of the stream of waste particles in movement away from said exit end for avoiding straying, hangup or recycling of the waste particles relative to said exit end;

(g) and means for applying a constant differential pressure throughout said fluid filled circuit during said analytical time span.

11. Means according to claim 10, wherein said sensing zone passage comprises a substantially accurately cylindrical bore in a member formed from polymeric material.

12. Means according to claim 11, wherein said member comprises a plug, and means having a recess receiving and supporting said plug with said sensing zone passage in aligned relation to said first passage.

13. Means according to claim 10, wherein said passages comprise a continuous bore through a member having an electrode at the entrance to said sensing zone passage and across which electrode the stream of longitudinally oriented particles pass into the sensing zone passage.

14. Means according to claim 10, wherein said first elongate passage is defined in a porous member through the wall of which a sheathing flow of fluid is adapted to pass into the first passage for enveloping the stream of particles in a particle free fluid sheath.

15. Apparatus according to claim 10, comprising means for enclosing said fluid sheathed core stream of waste particles in a second particle free fluid sheath from sheathing fluid surrounding said exit end, and said controlling means comprising a smoothly bellmouth shaped catcher port in coaxial adjacently spaced relation to said exit end for catching said fluid sheathed core stream from said exit end.

16. Apparatus according to claim 10, wherein the entrance end of said sensing zone passage has a flared smoothly contoured bellmouth receiver which opens cocentrically towards the downstream end of said first passage, means defining a chamber filled with particle-free sheathing fluid and enclosing a conically tapered tip terminating in a sharp edged rim at said downstream end of said first passage and from which the filamentary particle stream from said first passage discharges isokinetically coaxially toward and is received in said bellmouth receiver and thus in said sensing zone passage enveloped in sheathing fluid from said chamber.

17. Apparatus according to claim 10, wherein said means for generating electrical signals provides substantially trapezoidal pulses in response to the particles traversing the length of said sensing zone, and means for identifying the shape parameters of the particles.

18. Apparatus according to claim 10, wherein said means for generating electrical signals provides substantially trapezoidal pulses in response to the particles traversing the length of said sensing zone, and means by which the pulse shapes, particle length as well as particle shape are identified.

19. Apparatus according to claim 10, wherein said means for generating electrical signals provides substantially trapezoidal pulses in response to the particles traversing the length of particles, and means for determining pulse duration and volume of particles by pulse amplitude.

20. Apparatus according to claim 10, wherein said means for generating electrical signals provides substantially trapezoidal pulses in response to the particles traversing the length of said sensing zone, and means for pulse shape discrimination between particles of prolate, oblate and orthospheroid shapes is attained.

* * * * *